Jan. 24, 1950 E. S. BOERNER Plant Pat. 915
ROSE PLANT
Filed Dec. 7, 1948
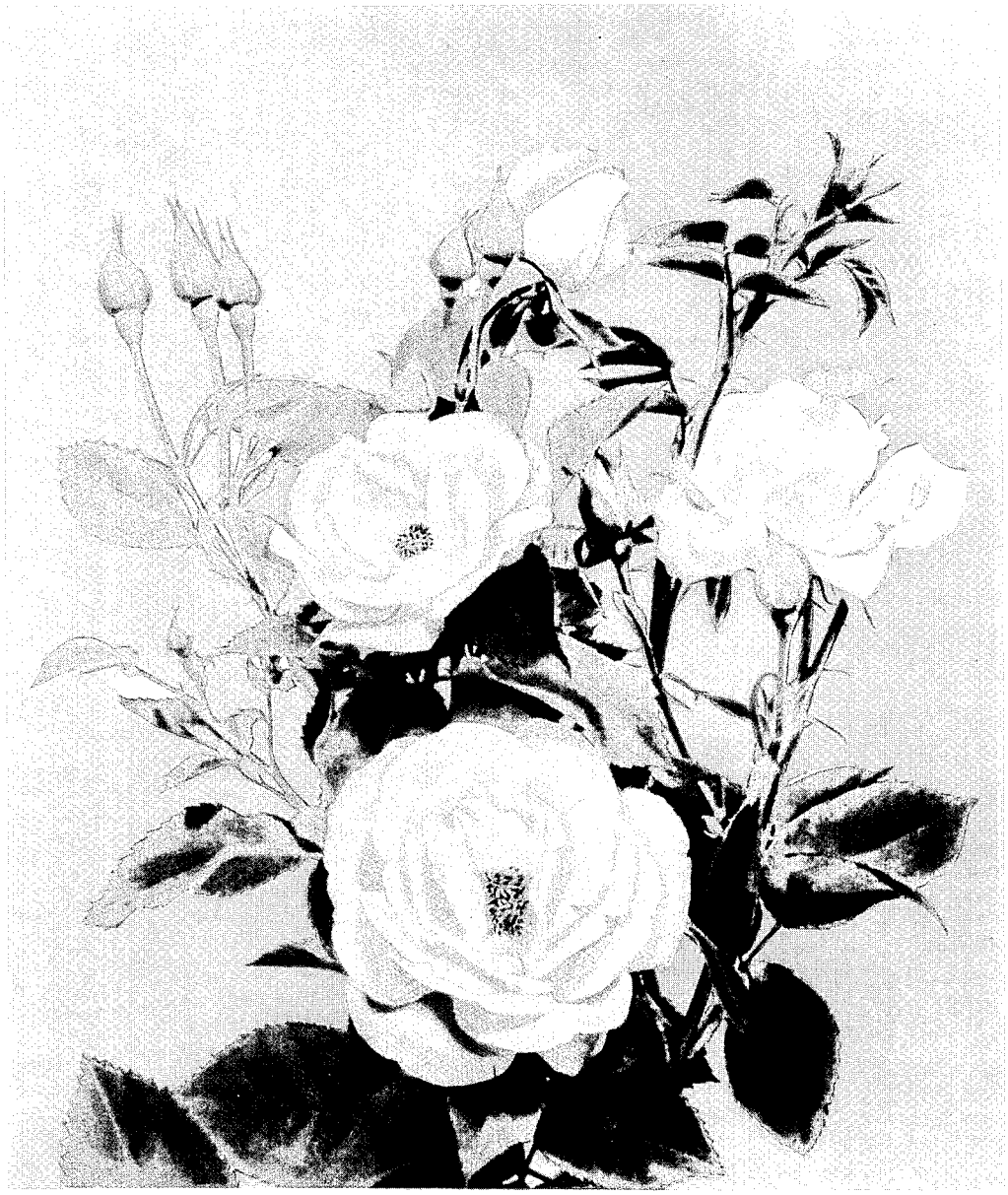
Inventor
E. S. Boerner
By Robbins Cobb
Attorneys.

Patented Jan. 24, 1950

Plant Pat. 915

UNITED STATES PATENT OFFICE

915

ROSE PLANT

Eugene S. Boerner, Newark, N. Y., assignor to Jackson & Perkins Company, Newark, N. Y., a corporation of New York Application December 7, 1948, Serial No. 63,875

1 Claim. (Cl. 47—61)

This invention relates to a new and distinct variety of rose plant of the Floribunda class, the result of selective crossing of known varieties to obtain a combination of desirable traits and characteristics.

This new variety is characterized as to novelty first, by the brilliant two-tone effect of its flowers and the habit of constant blooming in clusters of from three to ten flowers, the stamens of which show a shading quite unusual in roses. The value of this new variety is increased by its vigor of growth which is much greater than its pollen parent but less than its seed parent.

Asexual reproduction of this new variety shows the foregoing characteristics come true to form and are established.

In the accompanying drawing are illustrated specimens of this new variety at different stages of development from bud to full open bloom and in the two dominantly contrasting colors herein more specifically described.

The following is a detailed description of the new variety, color terminology being in accordance with Ridgway's Color Standards and Nomenclature:

Parentage: Seedling.

*Seed parent.*—"McGredy's Pillar" (unpatented).

*Pollen parent.*—"Pinocchio" (Pl. Pat. No. 484).

Classification: Botanic—large flowered polyantha. Commercial—Floribunda.

*Flower*

Observations made at Newark, New York, in the month of September in the afternoon.

Blooming habit: Recurrent—continuous.

Bud:

*Size.*—Medium.

*Form.*—Ovoid. Is not affected by wet or hot weather.

*Color.*—When sepals first divide—Carmine, Plate 1; when petals begin to unfurl—Tyrian Rose, Plate 12; when half blown—inside of petals—Tyrian Rose, Plate 12, lightening to Rose Color, Plate 12, in the lower half of the petal; reverse of petals—Rose Color, Plate 12, outer petals center Naphthalene Yellow, Plate 16.

*Sepals.*—Branched, "hood" above bud. Curl back when petals begin to unfurl. Color—inside—Kildare Green, Plate 31; outside—Parrot Green, Plate 6.

*Calyx.*—Shape—pear. Size—small. Aspect—smooth. Odor when rubbed—none. Color—Parrot Green, Plate 6.

*Peduncle.*—Length—long. Aspect—prickly. Color—Scheele's Green, Plate 6. Strength—erect; slender.

*Opening.*—Opens up well. Is not affected by adverse weather conditions.

Bloom:

*Size.*—Medium. Average size when fully expanded, 3" to 3½".

*Borne.*—In irregular clusters.

*Stems.*—Medium length; strong.

*Form.*—When first open—cupped. Permanence—retains its form to the end, flattens some.

*Petalage.*—Double (full but open center). Number of petals under normal conditions, 18 to 20.

*Color.*—Center of flower—Tyrian Rose, Plate 12. Outer petals—Rose Color, Plate 12. Base of petals (aiglet)—Light Greenish Yellow, Plate 5. Inside of petals—Tyrian Rose, Plate 12, edges lightened by Rose Color, Plate 12, in the center with the Light Greenish Yellow, Plate 5, from the aiglet overcasting the lower half of the petal. Reverse of petals—Straw Yellow, Plate 16, and the upper half of the petal shaded with Rose Color, Plate 12. General tonality from a distance—Rose Color, Plate 12.

*Discoloration.*—General tonality at end of first day—Rose Red, Plate 12. Second day—Tyrian Rose, Plate 12. Third day—Rose Color, Plate 12.

Petals:

*Texture.*—Leathery. Is not affected by wet or hot weather.

*Appearance.* — Inside — satiny; outside—shiny.

*Form.*—Oval.

*Arrangement.*—Imbricated (regularly arranged shingle-like). Petaloids in center—few; small.

*Persistence.*—Drop off cleanly.

*Fragrance.*—Slight. Nature—fruity (Russet apple).

*Lasting quality.*—On the plant—long; as cut flower—fair.

Genital organs:

*Stamens, anthers.*—Medium size; many. Color—Raw Sienna, Plate 3. Arrangement—regular around styles.

*Stamens, filaments (threads).* — Medium length. Color — Pale Lemon Yellow, Plate 4.

*Pollen.*—Color—Martius Yellow, Plate 4.
*Styles.*—Bunched uneven length; medium length; thin.
*Stigmas.*—Color—Pinard Yellow, Plate 4.
*Ovaries.*—All enclosed in calyx.

*Plant*

Foliage: 3 to 5 leaflets.
*Size.*—Medium.
*Quantity.*—Abundant.
*Color.*—New foliage: upper side—Oil Green, Plate 5, serrations Oxblood Red, Plate 1; under side—Yellowish Oil Green, Plate 5, with Oxblood Red, Plate 1, overcasting and serrations Oxblood Red, Plate 1; old foliage—upper side—Spinach Green, Plate 5; under side—Bice Green, Plate 17.
*Shape.*—Oval pointed.
*Texture.* — Upper side — glossy; smooth; under side—smooth. Ribs and veins—ordinary.
*Edge.*—Serrated (saw toothed).
*Serration.*—Single; small.
*Leaf stem.*—Color—Lettuce Green, Plate 5. Under side—prickles.
*Stipules.*—Long; bearded.
*Disease resistance.*—Resistant.

Wood:
*New wood.*—Color—Lettuce Green, Plate 5. Bark—smooth.
*Old wood.*—Color—Spinach Green, Plate 5. Bark—smooth.

Thorns:
*Thorns.*—Quantity: On main stalks from base—ordinary; on laterals from stalk—few. Form—flat base; long; hooked downward. Color when young—Light Lumiere Green, Plate 17. Position—irregular.
*Prickles.*—Quantity: On main stalks—few; on laterals — none. Color — Pale Glass Green, Plate 31.
*Short needles.*—None.

I claim:

A new and distinct variety of polyantha rose plant, characterized as to novelty by the brilliant contrasting color effect of its blooms; its habit of constant blooming in clusters of from three to ten flowers; the unique color shading of the stamens of said flowers and the habit of vigorous growth of the plant, substantially as shown and described.

EUGENE S. BOERNER.

No references cited.